US010055834B2

(12) United States Patent
Nukada

(10) Patent No.: US 10,055,834 B2
(45) Date of Patent: Aug. 21, 2018

(54) PATTERN INSPECTION APPARATUS, PATTERN IMAGING APPARATUS, AND PATTERN IMAGING METHOD

(71) Applicant: NuFlare Technology, Inc., Yokohama-shi (JP)

(72) Inventor: Hideki Nukada, Yokohama (JP)

(73) Assignee: NuFlare Technology, Inc., Yokohama-shi (JP)

(*) Notice: Subject to any disclaimer, the term of this patent is extended or adjusted under 35 U.S.C. 154(b) by 184 days.

(21) Appl. No.: 15/224,807

(22) Filed: Aug. 1, 2016

(65) Prior Publication Data

US 2017/0039699 A1    Feb. 9, 2017

(30) Foreign Application Priority Data

Aug. 4, 2015   (JP) ................................. 2015-154115

(51) Int. Cl.
*G06T 7/00*    (2017.01)
*G06T 7/60*    (2017.01)
*H04N 17/00*   (2006.01)

(52) U.S. Cl.
CPC ............ *G06T 7/0008* (2013.01); *G06T 7/001* (2013.01); *G06T 7/602* (2013.01); *H04N 17/002* (2013.01); *G06T 2207/30148* (2013.01)

(58) Field of Classification Search
CPC ....... G06T 7/0008; G06T 7/001; G06T 7/602; G06T 2207/30148; H04N 17/002
See application file for complete search history.

(56) References Cited

U.S. PATENT DOCUMENTS 5,502,564 A * 3/1996 Ledger .................. G01B 11/06
                                                    356/503
6,982,793 B1 * 1/2006 Yang .................... G03F 7/70633
                                                    356/401

(Continued)

FOREIGN PATENT DOCUMENTS

JP       2006-266864 A     10/2006
KR    10-2015-0052790 A     5/2015
WO     WO 02/080185 A1    10/2002

OTHER PUBLICATIONS

Korean Office Action dated Oct. 23, 2017 in Patent Application No. 10-2016-0098733 (with English translation).

*Primary Examiner* — Mia M Thomas
(74) *Attorney, Agent, or Firm* — Oblon, McClelland, Maier & Neustadt, L.L.P.

(57) ABSTRACT

A pattern inspection apparatus includes a first stage to mount an inspection target object, located at the position displaced from the gravity center of the first stage, first and second two-dimensional scales on the first stage and opposite each other with respect to the gravity center, a second stage under a region overlapping with the gravity center of the first stage and not overlapping with the target object, to support and move the first stage, a calculation processing circuitry to calculate the position of the inspection target object, using position information measured by the first and second two-dimensional scales, a sensor to capture an optical image of a pattern on the inspection target object in the state where the first stage on which the inspection target object is mounted is moving, and a comparison unit to compare, for each pixel, the optical image with a corresponding reference image.

10 Claims, 9 Drawing Sheets

(56) References Cited

U.S. PATENT DOCUMENTS

| | | | | |
|---|---|---|---|---|
| 7,564,545 B2* | 7/2009 | Stokowski | ............. | G03F 7/705 356/237.5 |
| 8,170,072 B2* | 5/2012 | Kawaguchi | ........ | B23K 26/0608 372/101 |
| 9,535,015 B2* | 1/2017 | Isomura | ................ | G06T 7/0008 |
| 2002/0109090 A1* | 8/2002 | Nakasuji | ................ | B82Y 10/00 250/311 |
| 2003/0139838 A1* | 7/2003 | Marella | .................. | G01N 21/55 700/110 |
| 2004/0032581 A1* | 2/2004 | Nikoonahad | .......... | G01N 21/55 356/237.2 |
| 2005/0051724 A1* | 3/2005 | Nakasuji | ............. | G01N 23/2251 250/310 |
| 2007/0156379 A1* | 7/2007 | Kulkarni | ............. | G06F 17/5045 703/14 |
| 2007/0229814 A1* | 10/2007 | Yamaguchi | ............. | G03F 1/44 356/237.4 |
| 2007/0230770 A1* | 10/2007 | Kulkarni | ............. | G06F 17/5045 382/149 |
| 2007/0288219 A1* | 12/2007 | Zafar | ........................ | G03F 1/84 703/14 |
| 2009/0140390 A1* | 6/2009 | Nishiura | ............... | H01L 29/045 257/615 |
| 2009/0206257 A1* | 8/2009 | Gunji | ...................... | H01J 37/28 250/310 |
| 2010/0060890 A1* | 3/2010 | Tsuchiya | ............... | G01N 21/956 356/237.5 |
| 2011/0255770 A1* | 10/2011 | Touya | ................ | G01N 21/9503 382/144 |
| 2012/0326016 A1* | 12/2012 | Ishizuka | ............ | G01D 5/2455 250/231.1 |
| 2013/0216120 A1* | 8/2013 | Inoue | .................... | G06T 7/0004 382/144 |
| 2013/0322737 A1* | 12/2013 | Murakami | ............... | G06T 7/001 382/149 |
| 2014/0231813 A1* | 8/2014 | Oda | .................. | H01L 21/02532 257/66 |
| 2014/0254913 A1* | 9/2014 | Pang | ....................... | G03F 1/70 382/144 |
| 2015/0125066 A1* | 5/2015 | Isomura | .................. | G06T 7/001 382/149 |
| 2016/0267648 A1* | 9/2016 | Yamashita | ............... | G06T 5/009 |
| 2016/0305892 A1* | 10/2016 | Tsuchiya | ............. | G01N 21/956 |
| 2017/0032177 A1* | 2/2017 | Suenaga | ........... | G06K 9/00208 |
| 2017/0316557 A1* | 11/2017 | Inoue | ..................... | G06T 7/001 |
| 2017/0352140 A1* | 12/2017 | Isomura | ................. | G06T 7/001 |

* cited by examiner

A-A

B-B

PATTERN INSPECTION APPARATUS, PATTERN IMAGING APPARATUS, AND PATTERN IMAGING METHOD

CROSS-REFERENCE TO RELATED APPLICATION

This application is based upon and claims the benefit of priority from the prior Japanese Patent Application No. 2015-154115 filed on Aug. 4, 2015 in Japan, the entire contents of which are incorporated herein by reference.

BACKGROUND OF THE INVENTION

Field of the Invention

Embodiments of the present invention relate generally to a pattern inspection apparatus, a pattern imaging apparatus, and a pattern imaging method. More specifically, embodiments of the present invention relate, for example, to a pattern inspection technique for inspecting pattern defects of an object serving as a target workpiece or "sample" used in manufacturing semiconductor devices, and to an inspection apparatus for inspecting defects of a minute pattern formed on a photomask, wafer, or liquid crystal substrate used in manufacturing semiconductor elements or liquid crystal displays (LCDs).

Description of Related Art

In recent years, with the advance of high integration and large capacity of large-scale integration (LSI) circuits, the line width (critical dimension) required for circuits of semiconductor elements is becoming progressively narrower. Such semiconductor elements are manufactured by circuit formation of exposing and transferring a pattern onto a wafer by means of a reduced projection exposure apparatus known as a stepper while using an original or "master" pattern (also called a mask or a reticle, hereinafter generically referred to as a mask) with a circuit pattern formed thereon. Then, in fabricating a mask used for transfer printing such a fine circuit pattern onto a wafer, a pattern writing apparatus capable of writing or "drawing" fine circuit patterns by using electron beams needs to be employed. Pattern circuits may be written directly on the wafer by the pattern writing apparatus. Also, a laser beam writing apparatus that uses laser beams in place of electron beams for writing a pattern is under development.

Since LSI manufacturing requires a tremendous amount of manufacturing cost, it is crucial to improve its yield. However, as typified by a 1-gigabit DRAM (Dynamic Random Access Memory), the scale of patterns configuring an LSI is in transition from on the order of submicrons to nanometers. One of major factors that decrease the yield of the LSI manufacturing is due to pattern defects on the mask used for exposing and transfer printing an ultrafine pattern onto a semiconductor wafer by the photolithography technology. In recent years, with miniaturization of dimensions of LSI patterns formed on a semiconductor wafer, dimension to be detected as a pattern defect has become extremely small. Therefore, a pattern inspection apparatus for inspecting defects on a transfer mask used in manufacturing LSI needs to be more highly accurate.

As an inspection method, there is known a method of comparing an optical image obtained by imaging a pattern formed on a target object or "sample" such as a lithography mask at a predetermined magnification by using a magnification optical system with design data or an optical image obtained by imaging the same pattern on the target object. For example, the methods described below are known as pattern inspection methods: the "die-to-die inspection" method that compares data of optical images of identical patterns at different positions on the same mask; and the "die-to-database inspection" method that inputs, into an inspection apparatus, writing data (design pattern data) generated by converting pattern-designed CAD data to a writing apparatus specific format to be input to the writing apparatus when a pattern is written on the mask, generates design image data (reference image) based on the input writing data, and compares the generated design image data with an optical image (serving as measurement data) obtained by imaging the pattern. In such inspection methods for use in the inspection apparatus, a target object is placed on the stage so that a light flux may scan the target object as the stage moves in order to perform an inspection. Specifically, the target object is irradiated with a light flux from the light source through the illumination optical system. Light transmitted through the target object or reflected therefrom forms an image on a sensor through the optical system. The image captured by the sensor is transmitted as measurement data to the comparison circuit. After performing position adjustment of images, the comparison circuit compares measurement data with reference data in accordance with an appropriate algorithm, and determines that there exists a pattern defect if the compared data are not identical.

In the inspection apparatus, the target object on the stage is irradiated with an inspection light, and its transmitted light or reflected light is input into the optical system. Since the region where the target object is placed of the stage serves as an optical path, it is difficult to arrange devices of a stage driving system in the region. Therefore, a cantilever support structure has been employed as a stage driving system. Accordingly, there is a problem that yawing of the stage at the driving time becomes large. Consequently, there is a problem that rotational deviation of the target object becomes large. Now, as a method for detecting the position of the stage, a laser length measuring method using a laser interferometer is known, for example. Then, x and y positions of the target object and the rotation angle of the target object are calculated using a result of the laser length measuring. However, laser beams are affected by fluctuation of air. Therefore, it is necessary to average the result of the laser length measuring, with spending a predetermined time. Thus, it is difficult for the laser length measuring method to rapidly and highly accurately perform position measurement. In order to conduct an inspection with high precision, it is desired to reduce rotational deviation of the target object due to the yawing of the stage at the driving time, and even when rotational deviation occurs, it is desired to rapidly and highly precisely measure the amount of rotational deviation.

Although differing from the inspection apparatus, there is disclosed a structure in which a wafer is placed in the center of the stage and the gravity center of the wafer stage is located on the working point of thrust in the x axis direction in order to suppress the biased load of the stage of the exposure apparatus, and the stage position is measured by a laser length measuring method (for example, refer to International Publication WO 02/080185A1). However, as described above, since the region where the target object is placed serves as an optical path in the inspection apparatus, it is difficult to arrange a mask in the center of the stage whose gravity is located on the working point of thrust in the x axis direction. Moreover, as described above, it is difficult to perform position measurement rapidly and highly precisely by using the laser length measuring method.

BRIEF SUMMARY OF THE INVENTION

According to one aspect of the present invention, a pattern inspection apparatus includes a first stage configured to mount a target object to be inspected on which a pattern is formed and which is located at a position displaced from a gravity center of the first stage, a first two-dimensional scale and a second two-dimensional scale arranged to be on the first stage and opposite each other with respect to a position of the gravity center of the first stage, a second stage arranged to be under a region overlapping with the gravity center of the first stage and not overlapping with the target object mounted on the first stage, and configured to support and move the first stage, a calculation processing circuitry configured to calculate a position of the target object to be inspected, using position information measured by the first two-dimensional scale and the second two-dimensional scale, an illumination optical system configured to illuminate the target object to be inspected, with an inspection light, a sensor configured to capture an optical image of the pattern formed on the target object to be inspected, in a state where the first stage on which the target object to be inspected is mounted is moving, and a comparison processing circuitry configured to compare, for each pixel, the optical image with a reference image corresponding to the optical image.

According to another aspect of the present invention, a pattern imaging apparatus includes a first stage configured to mount a target object on which a pattern is formed and which is located at a position displaced from a gravity center of the first stage, a first two-dimensional scale and a second two-dimensional scale arranged to be on the first stage and opposite each other with respect to a position of the gravity center of the first stage, a second stage arranged to be under a region overlapping with the gravity center of the first stage and not overlapping with the target object mounted on the first stage, and configured to support and move the first stage, a calculation processing circuitry configured to calculate a position of the target object, using position information measured by the first two-dimensional scale and the second two-dimensional scale, an illumination optical system configured to illuminate the target object with an inspection light, and a sensor configured to capture an optical image of the pattern formed on the target object.

According to yet another aspect of the present invention, a pattern imaging method includes capturing an optical image of a pattern formed on a target object which is mounted on a first stage and located at a position displaced from a gravity center of the first stage, measuring position information each from a first two-dimensional scale and a second two-dimensional scale which are arranged on the first stage and opposite each other with respect to a position of the gravity center of the first stage, and calculating a position of the target object, using the position information each measured from the first two-dimensional scale and the second two-dimensional scale.

DETAILED DESCRIPTION OF THE INVENTION

First Embodiment

A first embodiment of the present invention describes an inspection apparatus which can reduce rotational deviation of the target object due to yawing of the stage at the driving time and can rapidly and highly precisely measure the amount of rotational deviation.

Figure 1:
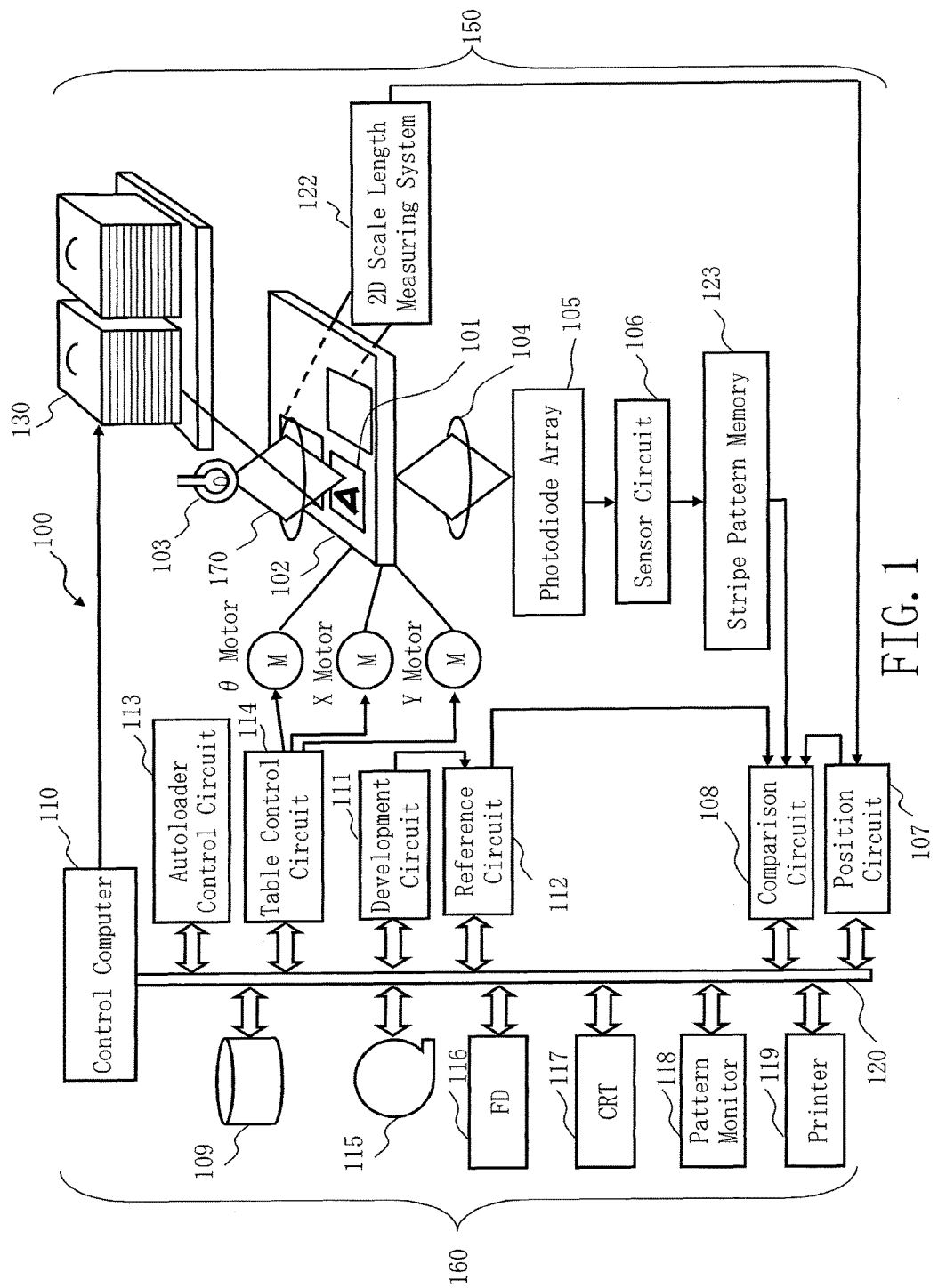
FIG. 1 illustrates a configuration of a pattern inspection apparatus according to a first embodiment.

FIG. 1 illustrates a configuration of a pattern inspection apparatus according to the first embodiment. As shown in FIG. 1, an inspection apparatus 100 that inspects defects of a pattern formed on a target object such as a mask includes an optical image acquisition unit 150 and a control system circuit 160 (control unit).

The optical image acquisition unit 150 includes a light source 103, an illumination optical system 170, an XYθ table 102 arranged movably, a magnifying optical system 104, a photodiode array 105 (an example of a sensor), a sensor circuit 106, a stripe pattern memory 123, and a two-dimensional (2D) scale length measuring system 122. The target object 101 and a plurality of two-dimensional (2D) scales are placed on the XYθ table 102. The target object 101 is, for example, an exposure photomask used for transfer printing a pattern onto a wafer. A pattern composed of a plurality of figure patterns to be inspected is formed on the photomask. The target object 101, for example, with its pattern forming surface facing downward, is arranged on the XYθ table 102.

In the control system circuit 160, a control computer 110 is connected, through a bus 120, to a position circuit 107, a comparison circuit 108, a development circuit 111, a reference circuit 112, an autoloader control circuit 113, a table control circuit 114, a magnetic disk drive 109, a magnetic tape drive 115, a flexible disk drive (FD) 116, a CRT 117, a pattern monitor 118, and a printer 119. The sensor circuit 106 is connected to the stripe pattern memory 123 which is connected to the comparison circuit 108. The XYθ table 102 is driven by motors of X-, Y-, and θ-axis.

In the inspection apparatus 100, an inspection optical system of large magnification is composed of the light source 103, the XYθ table 102, the illumination optical system 170, the magnifying optical system 104, the photodiode array 105, and the sensor circuit 106. The XYθ table 102 is driven by the table control circuit 114 under the control of the control computer 110. The XYθ table 102 can be moved by a drive system such as a three-axis (X, Y, and θ) motor, which drives the table in the directions of x, y, and θ. For example, a linear motor can be used as each of these X, Y, and θ motors. The XYθ table 102 is movable in the horizontal direction and the rotation direction by the motors of the X-, Y-, and θ-axis. The movement position of the target object 101 placed on the XYθ table 102 is measured by the 2D scale length measuring system 122, and supplied to the position circuit 107.

Design pattern data (writing data) used as the basis of forming patterns on the target object 101 to be inspected is input from the outside of the inspection apparatus 100, and stored in the magnetic disk drive 109. Moreover, region data (region information) on a plurality of regions indicating a part of inspection region of the target object 101 to be inspected is input from the outside of the inspection apparatus 100, and stored in the magnetic disk drive 109.

FIG. 1 shows configuration elements necessary for describing the first embodiment. It should be understood that other configuration elements generally necessary for the inspection apparatus 100 may also be included therein.

A pattern formed on the target object 101 is irradiated with a laser beam (for example, DUV light), which is used as an inspection light and whose wavelength is shorter than or equal to that of the ultraviolet region, from the appropriate light source 103 through the illumination optical system 170. Light having passed through the target object 101 enters the photodiode array 105 (an example of a sensor) via the magnifying optical system 104 to form an optical image thereon.

Figure 2:
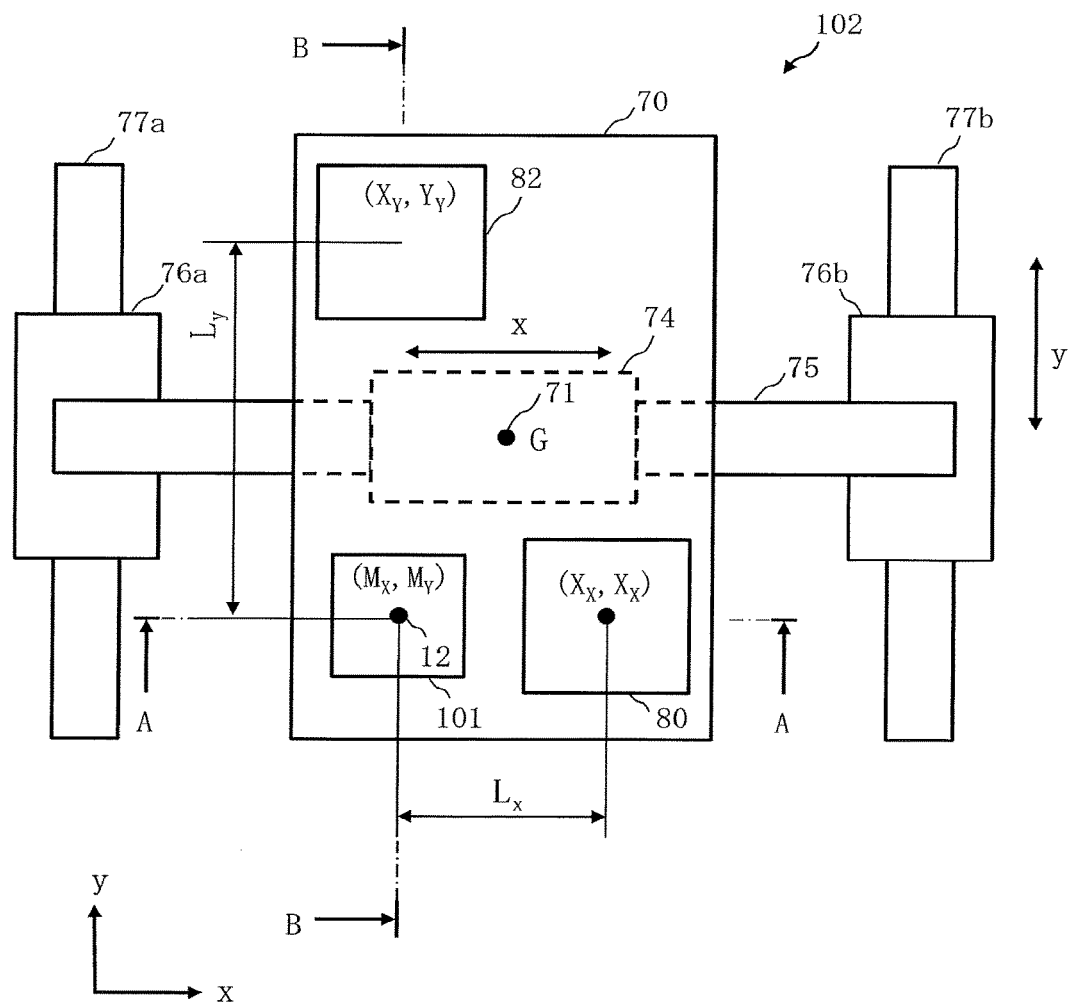
FIG. 2 is a top view showing the structure of an XYθ table, and the arrangement configuration between a 2D scale and a target object according to the first embodiment.

FIG. 2 is a top view showing the structure of the XYθ table, and the arrangement configuration between the 2D scale and the target object according to the first embodiment. As shown in FIG. 2, the XYθ table 102 includes a Zθ stage 70 (first stage), an x stage 74 (second stage), an x-axis guide rail 75, y stages 76a and 76b, and y-axis guide rails 77a and 77b. The linear stage in the x direction is configured using the x stage 74 and the x-axis guide rail 75. The linear stages in the y direction are configured using the y stages 76a and 76b and the y-axis guide rails 77a and 77b. Position adjustment of the Zθ stage 70 can also be controlled in the z direction (height direction or optical axis direction) in addition to travelling in the θ direction. For example, a plurality of piezoelectric elements (not shown) may be arranged to control the z direction position of the Zθ stage 70.

In the example of FIG. 2, the y stage 76a is placed on the y-axis guide rail 77a, to be movable (travelled) in the y direction, and the y stage 76b is placed on the y-axis guide rail 77b, to be movable (travelled) in the y direction. The y-axis guide rails 77a and 77b are arranged in parallel. Therefore, the y stages 76a and 76b travel in parallel. The x-axis guide rail 75 is arranged on the two y stages 76a and 76b in such a way as to straddle them. The x-axis guide rail 75 is arranged in the x direction to be orthogonal to the y-axis guide rails 77a and 77b. The x stage 74 is placed on the x-axis guide rail 75, to be movable (travelled) in the x direction. The Zθ stage 70 is placed on the x stage 74.

On the Zθ stage 70 according to the first embodiment, the target object 101 to be inspected, on which a pattern is formed, is placed at a position displaced from a gravity center 71(G) of the Zθ stage 70. In the example of FIG. 2, the target object 101 is located at the region on the -y side of the gravity center 71(G) of the Zθ stage 70. A 2D scale 80 (first two-dimensional scale) and a 2D scale 82 (second two-dimensional scale) are arranged on the Zθ stage 70 such that the relation of the scales 80 and 82 is opposite each other in direction with respect to the gravity center 71(G) of the Zθ stage 70. In other words, the two-dimensional scale 80 and the target object 101 are arranged such that the straight line in the inspection direction (x direction) passing through the position of the gravity center 71(G) of the Zθ stage 70 is not located between them. The two-dimensional scale 82 and the target object 101 are arranged such that the straight line in the inspection direction (x direction) passing through the position of the gravity center 71(G) of the Zθ stage 70 is located between them. The x stage 74 (second stage) is placed under the region overlapping with the gravity center 71(G) of the Zθ stage 70, and not overlapping with the target object 101 on the Zθ stage 70. At such region, the x stage 74 supports the Zθ stage 70 and moves the Zθ stage 70. Here, the Zθ stage 70 is moved in the x direction.

Figure 3:
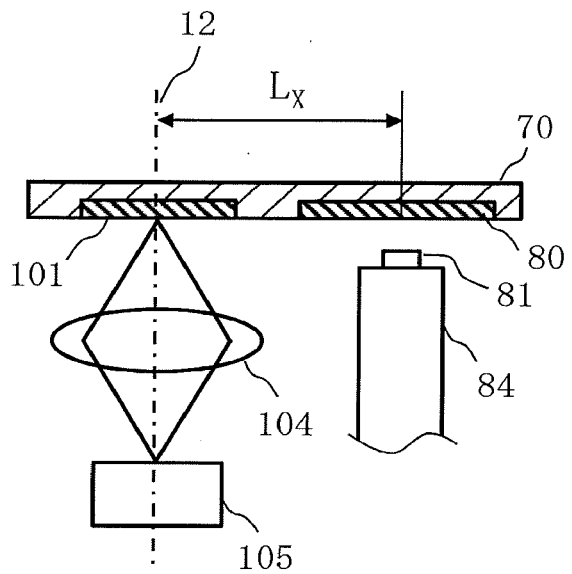
FIG. 3 is a sectional view, cut along the A-A line in FIG. 2, showing the arrangement configuration of a Zθ table, a 2D scale, and a target object according to the first embodiment.
Figure 4:
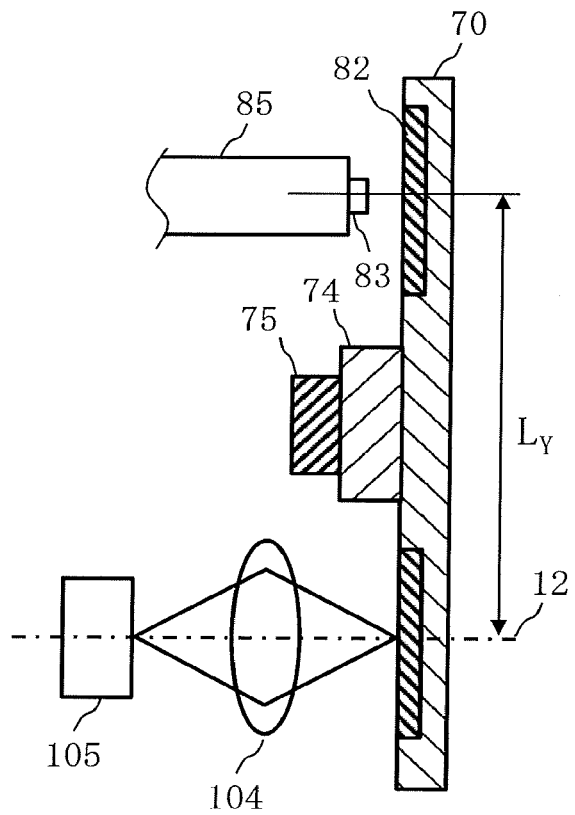
FIG. 4 is a sectional view, cut along the B-B line in FIG. 2, showing the arrangement configuration of the Zθ table, the 2D scale, and the target object according to the first embodiment.

FIG. 3 is a sectional view, cut along the A-A line in FIG. 2, showing the arrangement configuration of the Zθ table, the 2D scale, and the target object according to the first embodiment. FIG. 4 is a sectional view, cut along the B-B line in FIG. 2, showing the arrangement configuration of the Zθ table, the 2D scale, and the target object according to the first embodiment. As described above, the inspection light having passed through the target object 101 is input into the magnifying optical system 104. Therefore, as shown in FIGS. 3 and 4, the magnifying optical system 104 is arranged under the region where the target object 101 is placed in the region of the Zθ stage 70. In other words, the region where the target object 101 is placed on the surface of the Zθ stage 70 is located on an optical axis 12. As shown in FIG. 2, the 2D scale 80 is placed on one axis (x axis, in the case of FIG. 2) of the two mutually perpendicular axes (x axis and y axis) which are on the surface orthogonal to the optical axis 12 of the inspection light and intersect the optical axis 12. Then, the 2D scale 82 is placed on the other axis (y axis, in the case of FIG. 2). As described above, the target object 101 is arranged on the Zθ stage 70 such that the pattern forming surface of the target object 101 is facing downward. An opening penetrating the region where the target object 101 is placed should be formed in the Zθ stage 70, and at least a part of the outer periphery of the target object should be placed on the Zθ stage 70. As shown in FIGS. 3 and 4, the 2D scales 80 and 82 are arranged on (or "in") the Zθ stage 70 such that the scale forming surface (lower surface) is located on the same surface as the pattern forming surface (lower surface in FIGS. 3 and 4) of the target object 101.

As shown in FIG. 3, a detector 81 for detecting a position from the 2D scale 80 is arranged under the 2D scale 80. The detector 81 is fixed to a support table 84. The detector 81 is located at the position shifted in the x direction by $L_x$ from the optical axis 12 and not shifted in the y direction. In other words, the detector 81 is placed on one of the two mutually perpendicular axes which are on the surface orthogonal to the optical axis of the inspection light and intersect the optical axis, and placed immovably with respect to the optical axis. Thereby, the detector 81 can detect a value (position information) of the 2D scale 80, at the position shifted in the x direction by $L_x$ from the optical axis 12 and not shifted in they direction. For example, the detector 81 measures a position by irradiating a calibration grid of the 2D scale 80 with a laser beam by a light emitting device, receiving a diffracted light reflected from the 2D scale 80 by a light receiving device, and reading an interval between ruled lines on the surface of the 2D scale 80.

As shown in FIG. 4, a detector 83 for detecting a position from the 2D scale 82 is arranged under the 2D scale 82.

The detector 83 is fixed to a support table 85. The detector 83 is located at the position shifted in the y direction by $L_y$ from the optical axis 12 and not shifted in the x direction. In other words, the detector 83 is placed on the other one of the two mutually perpendicular axes which are on the surface orthogonal to the optical axis of the inspection light and intersect the optical axis, and placed immovably with respect to the optical axis. Thereby, the detector 83 can detect a value (position information) of the 2D scale 82, at the position shifted in the y direction by $L_y$ from the optical axis 12 and not shifted in the x direction. For example, the detector 83 measures a position by irradiating a calibration grid of the 2D scale 82 with a laser beam by a light emitting device, receiving a diffracted light reflected from the 2D scale 82 by a light receiving device, and reading an interval between ruled lines on the surface of the 2D scale 80.

The x stage 74 (second stage) is arranged under the region not overlapping with the 2D scales 80 and 82, as shown in FIG. 2. Thereby, the detector 81 can detect values of the whole region of the 2D scale 80 without being interfered by the x stage 74. Similarly, the detector 83 can detect values of the whole region of the 2D scale 82 without being interfered by the x stage 74.

Figure 5:
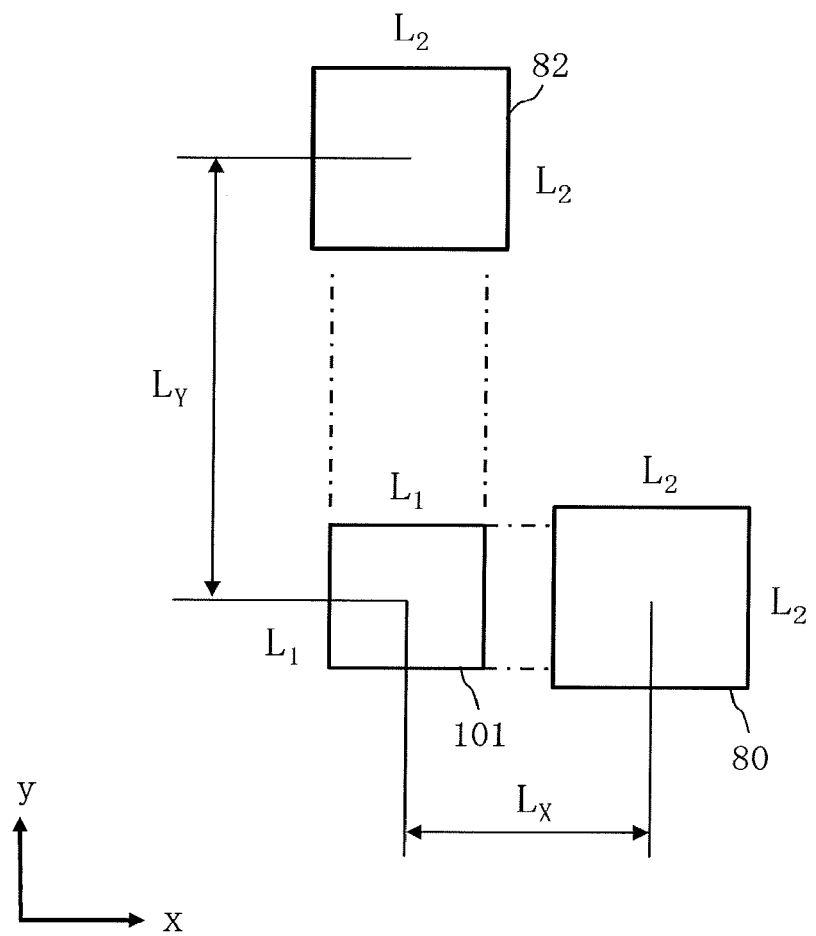
FIG. 5 shows an example of relative relationship between the sizes of the target object and the 2D scale according to the first embodiment.

FIG. 5 shows an example of relative relationship between the sizes of the target object and the 2D scale according to the first embodiment. The target object 101 is formed as a L1 square. By contrast, it is preferable for the 2D scales 80 and 82 to be formed as L2 squares whose width dimension is longer than the width dimension L1 of the target object 101 to be inspected. Thereby, the 2D scale 80 can be arranged such that each end of the side of the 2D scale 80 is more outward in the y direction than each end of the side of the target object 101 to be inspected. Moreover, as shown in FIG. 2, the 2D scale 80 can be arranged such that the center of the 2D scale 80 is shifted in the x direction by $L_x$ from the center of the target object 101 to be inspected, and not shifted in the y direction. Similarly, the 2D scale 82 can be arranged such that each end of the side of the 2D scale 82 is more outward in the x direction than each end of the side of the target object 101 to be inspected. Moreover, as shown in FIG. 2, the 2D scale 82 can be arranged such that the center of the 2D scale 82 is shifted in the y direction by $L_y$ from the center of the target object 101 to be inspected, and not shifted in the x direction. Thus, the 2D scale 80 can measure the position of the optical axis 12 wherever on the target object 101 to be inspected the optical axis 12 is located. In other words, the detector 81 can measure a position (coordinates (Xx, Yx)) from the 2D scale 80 wherever on the surface of the target object 101 the inspection position (coordinates (Mx, My)) is located. Similarly, the 2D scale 82 can measure the position of the optical axis 12 wherever on the target object 101 to be inspected the optical axis 12 is located. In other words, the detector 83 can measure a position (coordinates (Xy, Yy)) from the 2D scale 82 wherever on the surface of the target object 101 the inspection position (coordinates (Mx, My)) is located.

Figure 6:
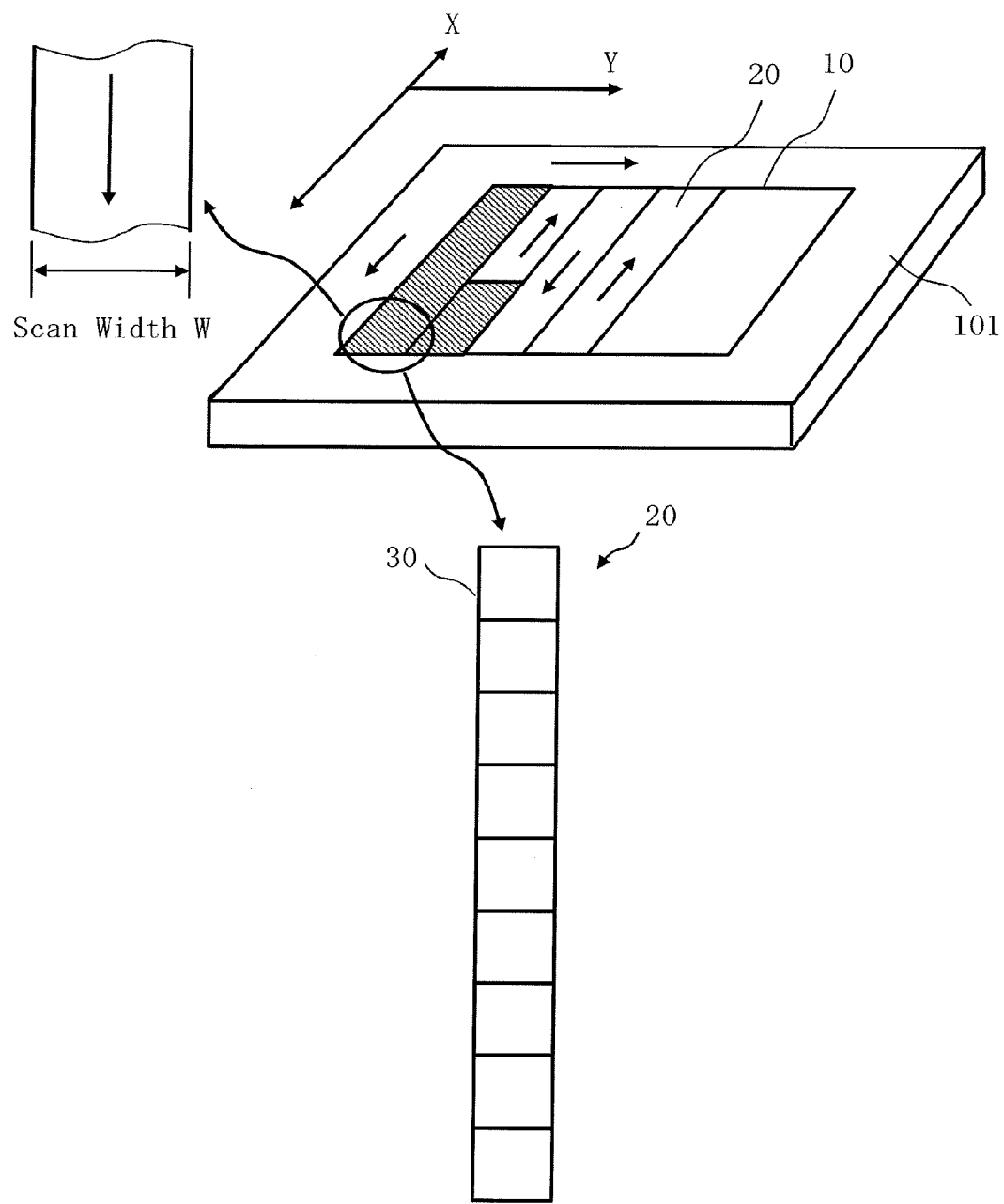
FIG. 6 is a conceptual diagram illustrating an inspection region according to the first embodiment.

FIG. 6 is a conceptual diagram illustrating an inspection region according to the first embodiment. As shown in FIG. 6, an inspection region 10 (entire inspection region) of the target object 101 is virtually divided into a plurality of strip-shaped inspection stripes 20 each having a scan width W in the y direction, for example. The inspection apparatus 100 acquires an image (strip region image) from each inspection stripe 20. That is, with respect to each of the inspection stripes 20, the inspection apparatus 100 captures an image of a figure pattern arranged in the stripe region concerned by using a laser light in the longitudinal direction (x direction) of the stripe region concerned. The photodiode array 105 which continuously moves relatively in the x direction acquires optical images because the Zθ stage 70 moves in the x direction by the movement of the x stage 74 in the XYθ table 120. The photodiode array 105 continuously captures optical images each having a scan width W as shown in FIG. 6. In other words, while moving relatively to the Zθ stage 70 (including the x stage 74), the photodiode array 105 being an example of a sensor captures optical images of patterns formed on the target object 101 by using an inspection light. According to the first embodiment, after capturing an optical image in one inspection stripe 20, the photodiode array 105 moves in the y direction to the position of the next inspection stripe 20 and similarly captures another optical image having a scan width W continuously while moving in the direction reverse to the last image capturing direction. Thereby, the image capturing is repeated in the forward(FWD) and backward(BWD) directions, namely changing the direction reversely when advancing and returning.

The direction of the image capturing is not limited to repeating the forward(FWD) and backward(BWD) movement. Images may be captured in a fixed one direction. For example, it is sufficient to repeat FWD and FWD, or alternatively, to repeat BWD and BWD.

Figure 7A:
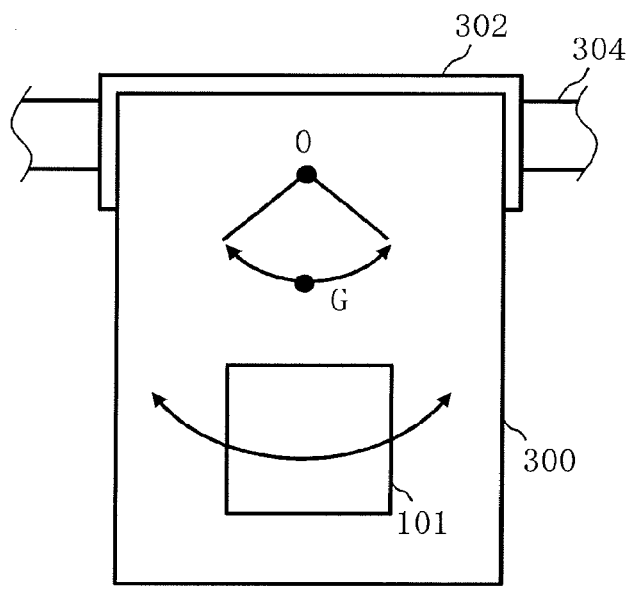
FIGS. 7A and 7B illustrate rotation of the Zθ stage according to the first embodiment.
Figure 7B:
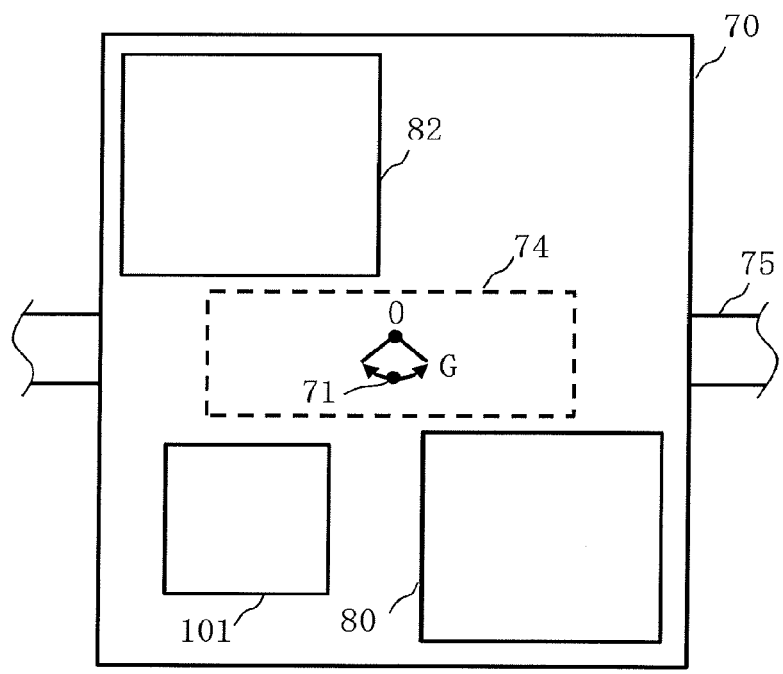

FIGS. 7A and 7B illustrate rotation of the Zθ stage according to the first embodiment. FIG. 7A shows yawing occurring in the case where the Zθ stage 300 is cantilever supported by the x stage 302 which travels on the x-axis guide rail 304. Since the gravity center G of the x stage 302 is located at a position displaced from the rotation center O on the x stage 302 serving as a working point, large yawing occurs in the Zθ stage 300 due to excitation force by acceleration and deceleration of the x stage 302. Consequently, large rotational deviation occurs in the target object 101. Similarly, large pitching occurs in the Zθ stage 300 due to excitation force by acceleration and deceleration of the x stage 302. By contrast, according to the first embodiment, as shown in FIG. 7B, the x stage 74 (second stage) is arranged under the region overlapping with the gravity center 71(G) of the Zθ stage 70. Therefore, since the excitation force due to acceleration and deceleration of the x stage 302 becomes small, yawing of the Zθ stage 70 can be made small. Consequently, rotational deviation of the target object 101 can be made small. Furthermore, pitching can also be made small. However, it is not necessarily possible to entirely eliminate the rotational deviation of the target object 101 resulting from the yawing. Then, according to the first embodiment, a rotational deviation θ of the target object 101 due to yawing is measured rapidly and highly accurately using the 2D scales 80 and 82.

Figure 8:
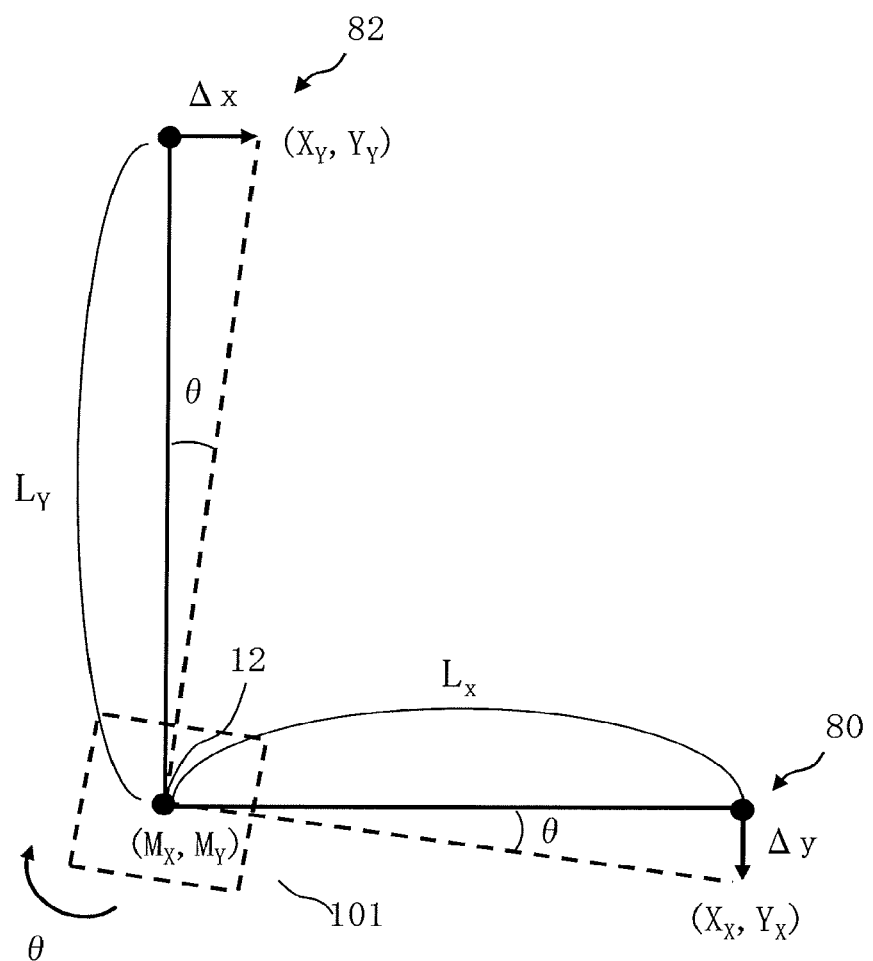
FIG. 8 illustrates a method for measuring a rotational deviation of the target object 101 according to the first embodiment.

FIG. 8 illustrates a method for measuring a rotational deviation of the target object 101 according to the first embodiment. FIG. 8 shows the case where a rotational deviation θ occurs with respect to the target object 101 due to yawing of the Zθ stage 70. When the rotational deviation θ occurs in the target object 101, the detection position (coordinates (Xx, Yx)) of the 2D scale 80 also deviates by the rotational deviation θ regarding the inspection position (coordinates (Mx, My)) of the target object 101 as the rotation center. Similarly, the detection position (coordinates (Xy, Yy)) of the 2D scale 82 also deviates by the rotational deviation θ regarding the inspection position (coordinates (Mx, My)) of the target object 101 as the rotation center. With respect to the x coordinate Xx of the 2D scale 80, there is only a small deviation that can be ignored when rotating. Similarly, with respect to the y coordinate Yy of the 2D scale 82, there is only a small deviation that can be ignored when rotating. Therefore, the coordinates (Mx, My) of the detection position on the target object 101 can be defined by the following equations (1) and (2):

$$Mx = Xx - Lx \quad (1)$$

$$My = Yy - Ly \quad (2)$$

The rotational deviation θ of the target object 101 can be defined by the following equation (3):

$$\begin{aligned}\theta &= \tan^{-1}(\Delta x / Ly) \\ &= \tan^{-1}\{(Xy - (Xx - Lx))/Ly\} \\ &\approx (Xy - (Xx - Lx))/Ly\end{aligned} \quad (3)$$

Similarly, the rotational deviation θ of the target object 101 can be defined by the following equation (4):

$$\begin{aligned}\theta &= \tan^{-1}(\Delta y / Lx) \\ &= \tan^{-1}\{((Yy - Ly) - Yx)/Lx\} \\ &\approx ((Yy - Ly) - Yx)/Lx\end{aligned} \quad (4)$$

According to the first embodiment, the 2D scales 80 and 82 are arranged opposite each other with respect to the position of gravity center of the Zθ stage 70. In other words, the 2D scales 80 and 82 are arranged opposite each other with respect to the x stage 74. Further expressed in another way, the target object 101 and the 2D scale 82 are arranged opposite each other with respect to the x stage 74. Therefore, it is possible to lengthen the distance Ly between the inspection position of the target object 101 and the detection position of the 2D scale 82. If comparing the equations (3) and (4), since Ly can be made greatly longer than Lx, Δx can be made larger than Δy even when defining the same rotation angle θ, thereby, the resolution of the rotation angle θ obtained by the equation (3) can be made larger than the one obtained by the equation (4). Accordingly, the rotational deviation θ of the target object 101 can be measured with great accuracy. Furthermore, according to the first embodiment, since the 2D scale is used, it is possible to avoid being affected by fluctuation of air, unlike the case of a laser interferometer. Therefore, when compared with measuring the position by a laser interferometer, measurement can be performed rapidly. Moreover, by not placing the laser interferometer which generates fluctuation of air, even when extending the Zθ stage 70 toward the region opposite to the region where the target object 101 is arranged, being opposite with respect to the x stage 74, the extended part of the stage can be secured as an arrangement space.

Now, pattern inspection is performed for the target object 101 by employing the position measurement method using the 2D scales 80 and 82.

Figure 9:
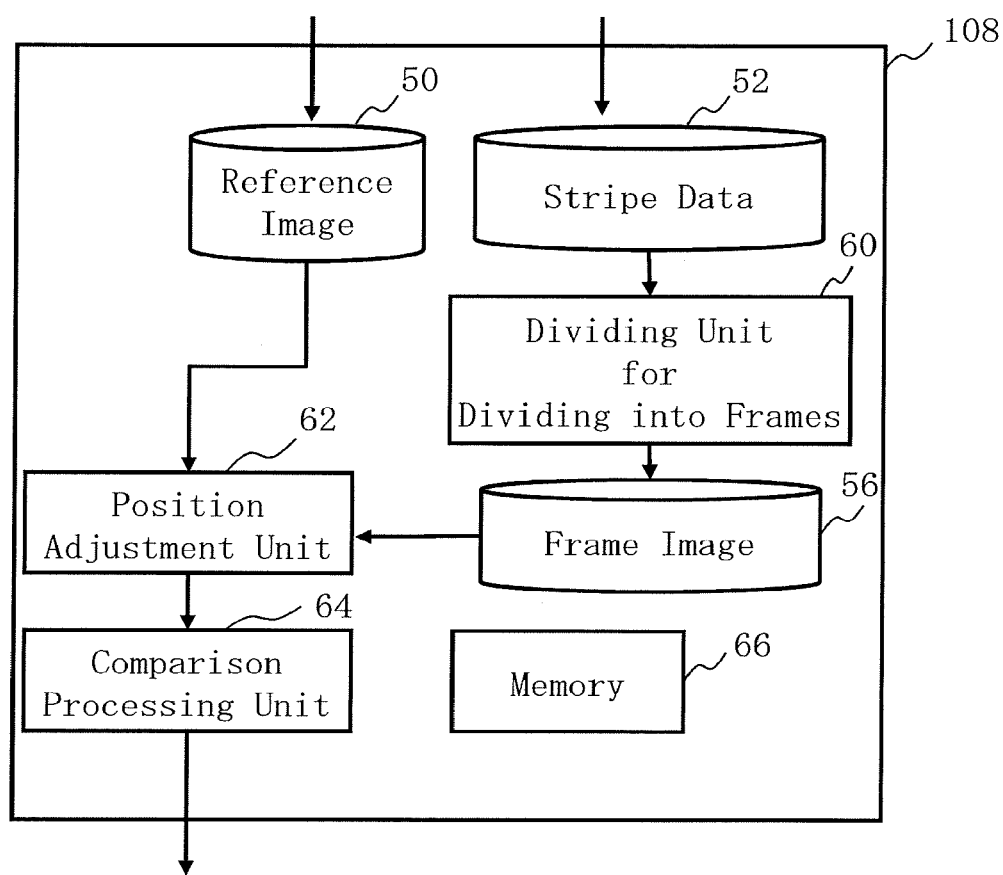
FIG. 9 is a block diagram showing an example of the internal structure of a comparison circuit according to the first embodiment.

FIG. 9 is a block diagram showing an example of the internal structure of a comparison circuit according to the first embodiment. As shown in FIG. 9, in the comparison circuit 108, there are arranged storage devices 50, 52, and 56, such as magnetic disk drives, a dividing unit 60 for dividing into frames, a position adjustment unit 62, a comparison processing unit 64, and a memory 66. Each " . . . unit", such as the dividing unit 60 for dividing into frames, the position adjustment unit 62, and the comparison processing unit 64, includes a processing circuitry. As the processing circuitry, for example, an electric circuit, computer, processor, circuit board, quantum circuit, or semiconductor device may be used. Each " . . . unit" may use a common processing circuitry (same processing circuitry), or different processing circuitries (separate processing circuitries). Input data required in the dividing unit 60 for dividing into frames, the position adjustment unit 62, and the comparison processing unit 64, and calculated results are stored in the memory 66 each time.

The optical image obtaining unit 150 acquires an optical image of the inspection stripe 20 of the photomask serving as the target object 101. Specifically, it operates as follows:

First, the x stage 74 and the y stage 76 are driven in order to move the Zθ stage 70 to the position at which a target inspection stripe 20 can be captured. A pattern formed on the target object 101 is irradiated with a laser beam (for example, DUV light) from the appropriate light source 103, which is used as an inspection light and whose wavelength is shorter than or equal to that of the ultraviolet region, through the illumination optical system 170. In other words, the illumination optical system 170 illuminates the target object 101 to be inspected with an inspection light. A light having passed through the target object 101 is focused, through the magnifying optical system 104, to form an image on the photodiode array 105 (an example of a sensor) as an optical image to be input thereinto. It is preferable to use, for example, a TDI (time delay integration) sensor, etc. as the photodiode array 105. In the state in which the Zθ stage 70 (first stage) with the inspection target object 101 thereon is moving, the photodiode array 105 (sensor) captures an optical image of a pattern formed on the inspection target object 101.

A pattern image focused/formed on the photodiode array 105 is photoelectrically converted by each light receiving element of the photodiode array 105, and further, analog-to-digital (A/D) converted by the sensor circuit 106. Then, pixel data for the inspection stripe 20 to be measured is stored in the stripe pattern memory 123. When imaging such pixel data (stripe region image), a dynamic range whose maximum gray level is defined as the case of, for example, 100% of the quantity of illumination light being incident is used as the dynamic range of the photodiode array 105. Moreover, when acquiring an optical image of the inspection stripe 20, the 2D scale length measuring system 122 inputs position information indicated by the 2D scales 80 and 82 detected by the detectors 81 and 83, and measures the position (coordinates (Xx, Yx)) indicated by the 2D scale 80 and the position (coordinates (Xy, Yy)) indicated by the 2D scale 82. Then, information on the position (coordinates (Xx, Yx)) indicated by the 2D scale 80 and the position (coordinates (Xy, Yy)) indicated by the 2D scale 82 is output to the position circuit 107. The position circuit 107 (calculation unit) calculates the position of the target object 101 to be inspected, by using position information measured by the 2D scales 80 and 82 (first and second two-dimensional scales). Such position information includes the x direction position Mx, y direction position My, and rotational deviation θ. Therefore, a stripe region image is an image captured in the state where the rotational deviation θ has occurred in the target object 101.

Then, the stripe region image is sent to the comparison circuit 108 together with data indicating the position of the target object 101 on the XYθ table 102 output from the position circuit 107. Measurement data (pixel data) is 8-bit unsigned data, for example, and indicates a gray level (light intensity) of brightness of each pixel. The stripe region image having been input into the comparison circuit 108 is stored in the storage device 52.

The dividing unit 60 for dividing into frames divides a stripe region image by a predetermined size (for example, by the same width as the scan width W) in the x direction so that a frame image of a target frame region 30 may be clipped from the stripe region image (optical image) of the inspection stripe 20. For example, it is divided into frame images each having 512×512 pixels. When clipping an image of the target frame region 30 from a stripe region image, the clipping is performed such that the rotational deviation θ is corrected. Thereby, the rotational deviation of the frame image of the target frame region 30 can be corrected. In other words, the stripe region image of each inspection stripe 20 is divided into a plurality of frame images (optical images) by the width being the same as that of the inspection stripe 20, for example, by the scan width W. By this processing, a plurality of frame images (optical images) corresponding to a plurality of frame regions 30 can be acquired. A plurality of frame images are stored in the storage device 56. Thus, data of one image (measured image) being one side to be compared for inspection is generated.

On the other hand, the development circuit 111 (an example of a design image generating unit) generates a design image by performing image development based on design pattern data used as the basis of pattern formation of the target object 101 to be inspected. Specifically, the development circuit ill reads design data from the magnetic disk drive 109 through the control computer 110. Each figure pattern in the region of a target frame 30 defined in the design data having been read is converted (image development) into image data of binary values or multiple values.

Basics of figures defined in design pattern data are, for example, rectangles or triangles. The design pattern data includes figure data (vector data) that defines the shape, size, position, and the like of each pattern figure by using information, such as coordinates (x, y) of the reference position of a figure, lengths of sides of the figure, and a figure code serving as an identifier for identifying the figure type, namely a rectangle, a triangle and the like.

When information on a design pattern, used as figure data, is input to the development circuit 111, the data is developed into data of each figure. Then, a figure code indicating the figure shape, figure dimensions and the like of the figure data are interpreted. Then, the development circuit 111 develops and outputs design image data of binary values or multiple values as a pattern to be arranged in a square in units of grids of predetermined quantization dimensions. In other words, the development circuit 111 reads design data, calculates the occupancy rate occupied by figures in a design pattern for each grid obtained by virtually dividing an inspection region into grids in units of predetermined dimensions, and outputs n-bit occupancy rate data. For example, it is preferable that one grid is set as one pixel. If one pixel is given resolution of $1/2^8$ (=$1/256$), $1/256$ small regions are allocated to the region of figures arranged in a pixel in order to calculate the occupancy rate in the pixel. Then, a design image data of 8-bit occupancy rate data is generated for each pixel. The design image data is output to the reference circuit 112.

The reference circuit 112 performs filter processing on the design image in order to generate a reference image.

Figure 10:
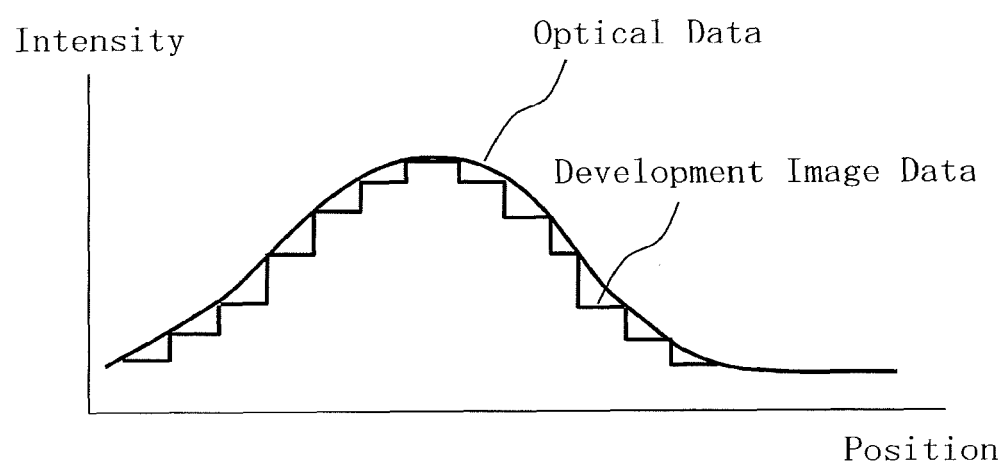
FIG. 10 illustrates filter processing according to the first embodiment.

FIG. 10 illustrates filter processing according to the first embodiment. Since the measurement data as an optical image obtained from the sensor circuit 106 is in a state affected by the filtering due to resolution characteristics of the magnifying optical system 104, an aperture effect of the photodiode array 105, or the like, in other words, in the analog state continuously changing, filter processing is also performed on reference design image data being image data on the design side having image intensity (gray value) represented by digital values in order to match the reference design image data with the measurement data. In this manner, a reference image to be compared with a frame image (optical image) is generated. The generated reference image is output to the comparison circuit 108 to be stored in the storage device 50. Thus, data of image (reference image) being the other side to be compared for inspection is generated.

The comparison circuit 101 (comparison unit) compares a frame image (optical image) with a reference image for each pixel. Specifically, first, the position adjustment unit 62 reads a frame image (optical image) to be compared from the storage device 56, and a reference image to also be compared from the storage device 50. Then, position adjustment is performed based on a predetermined algorithm. For example, the position adjustment is performed using a least-squares method. Then, the comparison processing unit 64 compares a frame image and a reference image for each pixel, based on predetermined determination conditions in order to determine whether there is a defect, such as a shape defect. As the determination conditions, for example, a predetermined algorithm is used, based on which a frame image and its corresponding reference image are compared with each other for each pixel in order to determine whether a defect exists or not. Then, the comparison result is output, and specifically should be output to the magnetic disk drive 109, magnetic tape drive 115, flexible disk drive (FD) 116, CRT 117, or pattern monitor 118, or alternatively, output from the printer 119.

As described above, according to the first embodiment, it is possible reduce a rotational deviation θ of the target object 101 due to yawing of the Zθ stage 70 at the driving time, and measure the amount of the rotational deviation θ rapidly and highly precisely. Therefore, inspection accuracy can be improved.

In the above description, what is described as a " . . . circuit" includes a processing circuitry. As the processing circuitry, for example, an electric circuit, computer, processor, circuit board, quantum circuit, or semiconductor device may be used. Each " . . . unit" may use a common processing circuitry (same processing circuitry), or different processing circuitries (separate processing circuitries). When configured by a computer and the like, programs are stored in a recording medium, such as a magnetic disk drive, magnetic tape drive, FD, ROM (Read Only Memory), etc.

Embodiments have been explained referring to specific examples described above. However, the present invention is not limited to these specific examples. For example, in Embodiments, although a transmitted illumination optical system using a transmitted light is described as the illumination optical system 170, it is not limited thereto. For example, a reflected illumination optical system using a reflected light may also be used. Alternatively, a transmitted light and a reflected light may be used simultaneously by way of combining a transmitted illumination optical system and a reflection illumination optical system.

In the example of FIG. 2, although the target object 101 is located at the 2D scale 80 side in both region sides of the Zθ stage 70, where the x stage 74 is located between the both region sides, it is not limited thereto. The target object 101 may also be located at the 2D scale 82 side.

While the apparatus configuration, control method, and the like not directly necessary for explaining the present invention are not described, some or all of them can be selectively used on a case-by-case basis when needed. For example, although description of the configuration of the control unit for controlling the inspection apparatus 100 is omitted, it should be understood that some or all of the configuration of the control unit can be selected and used appropriately when necessary.

In addition, any other pattern inspection apparatus and pattern inspection method that include elements of the present invention and that can be appropriately modified by those skilled in the art are included within the scope of the present invention.

Additional advantages and modification will readily occur to those skilled in the art. Therefore, the invention in its broader aspects is not limited to the specific details and representative embodiments shown and described herein.

Accordingly, various modifications may be made without departing from the spirit or scope of the general inventive concept as defined by the appended claims and their equivalents.

What is claimed is:

1. A pattern inspection apparatus comprising:
a first stage configured to mount a target object to be inspected on which a pattern is formed and which is located at a position displaced from a gravity center of the first stage;
a first two-dimensional scale and a second two-dimensional scale arranged to be on the first stage and opposite each other with respect to a position of the gravity center of the first stage;
a second stage arranged to be under a region overlapping with the gravity center of the first stage and not overlapping with the target object mounted on the first stage, and configured to support and move the first stage;
a calculation processing circuitry configured to calculate a position of the target object to be inspected, using position information measured by the first two-dimensional scale and the second two-dimensional scale;
an illumination optical system configured to illuminate the target object to be inspected, with an inspection light;
a sensor configured to capture an optical image of the pattern formed on the target object to be inspected, in a state where the first stage on which the target object to be inspected is mounted is moving; and
a comparison processing circuitry configured to compare, for each pixel, the optical image with a reference image corresponding to the optical image.

2. The apparatus according to claim 1, wherein the first two-dimensional scale is arranged on one of two mutually perpendicular axes which are on a surface orthogonal to an optical axis of the inspection light and intersect the optical axis, and the second two-dimensional scale is arranged on an other of the two mutually perpendicular axes.

3. The apparatus according to claim 1, wherein a width dimension of the first two-dimensional scale and the second two-dimensional scale is longer than a width dimension of the target object to be inspected.

4. The apparatus according to claim 1, wherein the second stage is arranged under a region not overlapping with the first two-dimensional scale and the second two-dimensional scale.

5. The apparatus according to claim 1, wherein the sensor receives a transmitted light having passed through the target object to be inspected.

6. The apparatus according to claim 1, further comprising:
a first detector arranged to be on one of two mutually perpendicular axes which are on a surface orthogonal to an optical axis of the inspection light and intersect the optical axis, and to be immovable with respect to the optical axis, and configured to detect position information from the first two-dimensional scale; and
a second detector arranged to be on an other of the two mutually perpendicular axes which intersect the optical axis, and to be immovable with respect to the optical axis, and configured to detect position information from the second two-dimensional scale.

7. The apparatus according to claim 1, wherein
the first two-dimensional scale and the target object to be inspected are arranged such that a straight line in an inspection direction passing through the position of the gravity center of the first stage is not located between the first two-dimensional scale and the target object to be inspected, and
the second two-dimensional scale and the target object to be inspected are arranged such that the straight line in the inspection direction passing through the position of the gravity center of the first stage is located between the second two-dimensional scale and the target object to be inspected.

8. A pattern imaging apparatus comprising:
a first stage configured to mount a target object on which a pattern is formed and which is located at a position displaced from a gravity center of the first stage;
a first two-dimensional scale and a second two-dimensional scale arranged to be on the first stage and opposite each other with respect to a position of the gravity center of the first stage;
a second stage arranged to be under a region overlapping with the gravity center of the first stage and not overlapping with the target object mounted on the first stage, and configured to support and move the first stage;
a calculation processing circuitry configured to calculate a position of the target object, using position information measured by the first two-dimensional scale and the second two-dimensional scale;
an illumination optical system configured to illuminate the target object with an inspection light; and
a sensor configured to capture an optical image of the pattern formed on the target object.

9. The apparatus according to claim 8, wherein the sensor receives a transmitted light having passed through the target object.

10. A pattern imaging method comprising:
capturing an optical image of a pattern formed on a target object which is mounted on a first stage and located at a position displaced from a gravity center of the first stage;
measuring position information each from a first two-dimensional scale and a second two-dimensional scale which are arranged on the first stage and opposite each other with respect to a position of the gravity center of the first stage; and
calculating a position of the target object, using the position information each measured from the first two-dimensional scale and the second two-dimensional scale.

* * * * *